United States Patent
Braman et al.

(10) Patent No.: US 11,718,847 B2
(45) Date of Patent: Aug. 8, 2023

(54) AMPLIFYING OLIGONUCLEOTIDES AND PRODUCING LIBRARIES OF DUAL GUIDE CONSTRUCTS

(71) Applicant: Agilent Technologies, Inc., Santa Clara, CA (US)

(72) Inventors: Jeffrey Carl Braman, Carlsbad, CA (US); Peter James Sheffield, Vista, CA (US); Holly Hogrefe, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1305 days.

(21) Appl. No.: 16/116,147

(22) Filed: Aug. 29, 2018

(65) Prior Publication Data
US 2020/0071690 A1 Mar. 5, 2020

(51) Int. Cl.
| C12N 15/10 | (2006.01) |
| C12N 15/11 | (2006.01) |
| C12Q 1/686 | (2018.01) |
| C12N 15/66 | (2006.01) |
| C12Q 1/6853 | (2018.01) |
| C40B 50/06 | (2006.01) |
| C40B 50/04 | (2006.01) |
| C40B 70/00 | (2006.01) |

(52) U.S. Cl.
CPC ..... *C12N 15/1065* (2013.01); *C12N 15/1068* (2013.01); *C12N 15/1096* (2013.01); *C12N 15/11* (2013.01); *C12N 15/66* (2013.01); *C12Q 1/686* (2013.01); *C12Q 1/6853* (2013.01); *C12N 2330/31* (2013.01); *C40B 50/04* (2013.01); *C40B 50/06* (2013.01); *C40B 70/00* (2013.01)

(58) Field of Classification Search
CPC .... C12N 15/11; C12N 15/1068; C12N 15/66; C12N 15/1065; C12N 15/1096; C12N 2330/31; C12Q 1/686; C12Q 1/6853
See application file for complete search history.

(56) References Cited

U.S. PATENT DOCUMENTS

| 5,948,663 | A | 9/1999 | Mathur |
| 6,183,997 | B1 | 2/2001 | Hogrefe |
| 6,444,428 | B1 | 9/2002 | Hogrefe |
| 6,734,293 | B1 | 5/2004 | Hogrefe et al. |
| 7,625,725 | B1 | 12/2009 | Hogrefe et al. |
| 7,932,070 | B2 | 4/2011 | Hogrefe et al. |
| 7,960,157 | B2 | 6/2011 | Borns |
| 9,181,534 | B1 | 11/2015 | Hogrefe et al. |
| 2017/0369870 | A1* | 12/2017 | Gill ...................... C12N 15/102 |

FOREIGN PATENT DOCUMENTS

WO 2016130697 8/2016

OTHER PUBLICATIONS

Von Ashen et al.; Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas; Clinical Chemistry 47:11, 1956-1961 (2001) (Year: 2001).*
Chen, X., et al., "Dual sgRNA-directed gene knockout using CRISPR/Cas9 technology in Caenorhabditis elegans," Scientific Reports, vol. 4, Article No. 7581 (2014), 7 pages. (DOI: 10.1038/srep07581).
Vidigal, J.A, et al., "Rapid and efficient one-step generation of paired gRNA CRISPR-Cas9 libraries," Nature Communications, vol. 6, Article No. 8083 (2015), 7 pages. (DOI: 10.1038/ncomms9083).
Glökler, J., et al., "Idiot-proof emulsion PCR", Lab Times, 2011, vol. 1, p. 50.
Hogrefe et al., Novel PCR Enhancing Factor Improves Perfrmance of Pfu DNA Polymerase, Strategies, 1997, vol. 10, pp. 93-96.
Lahr, D.J.G., et al., "Reducing the impact of PCR-mediated recombination in molecular evolution and environmental studies using a new-generation high-fidelity DNA polymerase," Biotechniques, 2009, vol. 47(4), 857-866.

* cited by examiner

*Primary Examiner* — Heather Calamita

(57) ABSTRACT

Methods and compositions are provided for amplifying a pool of oligonucleotides, such as dual guide oligonucleotide constructs comprising sequences encoding a first guide RNA segment and a sequence encoding a second guide RNA segment. An amplification mixture is formed comprising the pool of oligonucleotides, an amplification enzyme, deoxyribonucleotide triphosphates, and primers. The amplification mixture is thermocycled a sufficient number of times and under conditions to produce a library of oligonucleotide constructs. The present methods and compositions provide dual guide libraries, including libraries that are essentially free of scrambled library members.

17 Claims, 8 Drawing Sheets

AMPLIFYING OLIGONUCLEOTIDES AND PRODUCING LIBRARIES OF DUAL GUIDE CONSTRUCTS

CROSS-REFERENCE TO RELATED APPLICATIONS

None.

BACKGROUND OF THE INVENTION

Amplification methods such as polymerase chain reaction (PCR) are used in molecular biology to amplify a segment of DNA by generating copies of the segment. PCR methods generally rely on thermal cycling, where the DNA segment (or template), polymerase, primer, and deoxyribonucleoside triphosphates (dNTPs) are cycled through heating and cooling. The cycling permits repeated DNA denaturation, primer hybridization, and polymerase-driven DNA replication. Primers containing sequences complementary to a region of the DNA template, along with a DNA polymerase (e.g. Taq polymerase) are included in the mixture. As PCR progresses, the DNA copies serve as additional templates for replication, yielding a chain reaction in which the original DNA template can be exponentially amplified.

PCR is used in a variety of in vitro DNA synthesis applications, such as DNA sequencing, DNA amplification and mutagenesis. A variety of thermostable DNA polymerases with different activities are available. Because of the different properties of various polymerases, efforts have been made to modify, to alter, or to recombine various features of nucleic acid polymerases to develop new and useful variants of amplification enzymes.

For instance, Borns U.S. Pat. No. 7,960,157 (Agilent Technologies, Inc.) discloses novel blends of chimeric and non-chimeric thermostable DNA polymerases for use in PCR, DNA sequencing and mutagenesis protocols. They allow for PCR reactions with shorter extension times that will facilitate PCR amplification of genomic DNA templates and improve the efficacy of long PCR. Hogrefe et al. U.S. Pat. No. 7,932,070 (Agilent) discloses compositions comprising an enzyme mixture which comprises a first enzyme and a second enzyme, where the first enzyme comprises a DNA polymerization activity and the second enzyme comprises a 3'-5' exonuclease activity and a reduced DNA polymerization activity.

Molecular biology also makes use of enzymes that recognize, bind to and cleave nucleic acids at specific sites. CRISPR/Cas systems have been identified as programmable enzymes that recognize a specific sequence determined by the user. CRISPR/Cas systems employ non-coding RNA that is processed into short RNAs with CRISPR repeats serving as processing signals. These processed RNAs act as "guides", directing a Cas enzyme complexes to specific nucleic acid sites for cleavage. There are currently thousands of known CRISPR systems, and they are categorized into three major groups according to their associated Cas proteins. Among these, CRISPR systems characterized by the Cas9 protein are of great interest, in that Cas9 will cleave double strand DNA at a site targeted by the guide RNA. Much of the attention received by the Cas9 system is due to its activity in mammalian cells, thus enabling specific engineering of this genome.

Use of single guide pooled libraries for both gene knockout experiments (GeCKo) and CRISPRai (a=gene activation, i=inhibition) has transformed drug discovery research efforts by allowing researchers to identify genes and their products involved in disease progression. Single guide pooled libraries induce point mutations/missense mutations through a process referred to as the error prone DNA Non-Homologous End Joining (NHEJ) repair mechanism. The ability to simultaneously target virtually every known coding region of a gene has rapidly increased knowledge of those genes involved in any given biochemical pathway. This has allowed researchers to identify a handful of genes (for example, less than 50) out of the thousands of genes in the human genome for alteration. This technology is not limited to mammalian genomes but has been shown to be effective in many different species from bacteria to yeast and plants.

Genomic DNA can be exposed to pairs of guide RNA's that target different sites. For instance, a Cas9 nickase mutant can be employed with a pair of guide RNAs to introduce gRNA-targeted single-strand breaks in DNA instead of the double-strand breaks created by wild type Cas enzymes. Often the two gRNAs target opposite strands of the DNA in close proximity and effectively extends the number of specifically recognized bases at a target site. When combined with Cas9, the coexpression of two guides can be used to generate double-stranded breaks at target sites while minimizing damage at off-target loci. The ability to generate pooled libraries of CRISPR-Cas9 vectors expressing paired gRNA expands the potential applications of this technology for functional genomic screens. Dual guide pooled libraries represent an extension of single guide pooled libraries and differ by having two guides in the same expression cassette to ensure that predefined pairs of guides are expressed in the same cell.

Expression of two guide RNAs in a cell can be achieved by co-delivery of two single guide vectors, as noted in Chen et al., *Scientific Reports*, 4:7581 (DOI: 10.1038/srep07581). However, this results in two random guides being expressed which may target two potentially unrelated genes. Predefined dual paired guide libraries allow researchers to target pairs of target genes specifically.

Paired guide RNA CRISPR-Cas9 libraries are discussed in Vidigal et al. "Rapid and efficient one-step generation of paired gRNA CRISPR-Cas9 libraries", *Nature Communications* Vol. 6, Article number: 8083 (2015). Vidigal et al. reports that specific gRNA-pairs were cloned into an expression vector. An intermediate circularization-linearization step was used so that the two gRNAs were cloned downstream of independent U6 promoters in the final plasmid. Vidigal et al. also states that because the sequence of the two gRNAs paired in the dual-expression construct is determined at the oligonucleotide design step correct pairing of gRNAs for the same genomic locus in the resulting plasmid is ensured. Vidigal et al. sequenced plasmid DNA from 90 bacterial colonies and reported that 10% of clones contained chimeric inserts.

Vidigal et al. WO 2016/130697 discusses a method to build libraries expressing paired gRNAs. The authors state that the method may be used to expand potential applications of CRISPR-technology for in vitro and in vivo functional genomics.

SUMMARY OF THE INVENTION

The present disclosure provides methods for amplifying a pool of oligonucleotides, such as a pool of dual guide oligonucleotide constructs comprising sequences encoding a first guide RNA segment and a sequence encoding a second contiguous guide RNA segment. An amplification mixture is formed comprising the pool of oligonucleotides, an amplification enzyme, deoxyribonucleotide triphosphates, and primers. The amplification mixture is thermocycled a sufficient number of times and under thermocycling conditions to produce a library of double strand constructs. The present methods allow the production of dual guide libraries, including libraries that are essentially free of scrambled or mispaired dual guide library members.

As one aspect of the present invention, a method of amplifying a pool of oligonucleotides is provided. The method comprises providing a pool of oligonucleotides, wherein each of the oligonucleotides comprises a predefined pair of sequences encoding guide RNA segments. An amplification mixture is formed which comprises the pool of oligonucleotides, an amplification enzyme, deoxyribonucleotide triphosphates (dNTPs), and primers. The amplification mixture is cycled between a denaturing temperature, an annealing temperature, and optionally an extension temperature, a sufficient number of times to produce a library of oligonucleotide library members. Essentially all of the library members have one of the predefined pairs of sequences encoding guide RNA segments. For instance, a library is provided where at least 99.9%, alternatively at least 99.99%, of the library members are essentially free of mispaired sequences encoding guide RNA segments.

As additional aspects of the present invention, methods are provided to evaluate an oligonucleotide library. A pool of oligonucleotides is amplified according to the amplification methods described herein to form a library of oligonucleotide constructs. Thousands of library members are sequenced at once by massively parallel sequencing to determine whether the library comprises one or more library members having mispaired sequences encoding guide RNA segments, or a pair different from the predefined pairs in the pool of oligonucleotides. If 99.9% or greater of the library members are free of mispaired sequences, the library is then cloned into an appropriate vector for introduction into the test organism-system of choice. This process is far superior to the evaluation method of first cloning the library followed by laborious clone screening by any method to confirm appropriately paired guides.

These and other features and advantages of the present methods and compounds will be apparent from the following detailed description, in conjunction with the appended claims.

BRIEF DESCRIPTION OF THE DRAWINGS

The present teachings are best understood from the following detailed description when read with the accompanying figures. The features are not necessarily drawn to scale. Wherever practical, like reference numerals refer to like features.

DEFINED TERMINOLOGY

Figure 1:
FIG. 1 illustrates a dual guide oligonucleotide construct.

It is to be understood that the terminology used herein is for purposes of describing specific embodiments only and is not intended to be limiting. The defined terms are in addition to the technical and scientific meanings of the defined terms as commonly understood and accepted in the technical field of the present teachings.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.5 to 11.5. For example, "approximately the same" means that one of ordinary skill in the art considers the items being compared to be the same.

As used in the specification and appended claims, the terms "a," "an," and "the" include both singular and plural referents, unless the context clearly dictates otherwise. Thus, for example, "a moiety" includes one moiety and plural moieties. The terms "plurality" as used herein means two or more (or at least two), more particularly 3 or more (or at least 3), or 4, 5, 6, 8, 10, 15, 20, 30, 50, 70, 100, 500, 1000, 2000, 5000, 10000, 20000, 50000 or more. For example, 10, 100, 1000, 5000, 10000, 20000, 50000 or more different oligonucleotides may simultaneously be amplified by the present methods. The term "pair" as used herein generally refers to two, though it does not exclude the possibility of being two or more (or at least two), or three, four, or more.

As disclosed herein, several ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both limits, ranges excluding either or both of those included limits are also included in the invention.

A "nucleotide" refers to a sub-unit of a nucleic acid (whether DNA or RNA or analog thereof) which includes a phosphate group, a sugar group and a heterocyclic base, as well as analogs of such sub-units. Other groups (e.g., protecting groups) can be attached to any component(s) of a nucleotide. A "nucleoside" or "nucleoside moiety" refers to a nucleic acid subunit including a sugar group and a heterocyclic base, as well as analogs of such sub-units.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, acylated purines or pyrimidines, alkylated riboses or other heterocycles. Such modifications include, by way of examples, diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, or the like. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Modified nucleosides or nucleotides also include modifications on the internucleotide linkage or backbone moiety. "Analogs" refer to molecules having structural features that are recognized in the literature as being mimetics, derivatives, having analogous structures, or other like terms, and include, for example, oligonucleotides incorporating non-natural (not usually occurring in nature) nucleotides, unnatural nucleotide mimetics such as 2'-modified nucleosides, peptide nucleic acids, oligomeric nucleoside phosphonates, and any oligonucleotide that has added substituent groups, such as protecting groups or linking groups.

"Oligonucleotide" refers to a compound containing a plurality of nucleoside moiety subunits that are linked by internucleotide bonds. As such, the term also refers to a compound containing a plurality of nucleotide moiety subunits or residues. An oligonucleotide might contain ribonucleosides, or deoxyribonucleosides or a mixture thereof. An oligonucleotide may comprise natural and/or non-natural nucleosides, nucleoside analogs and modified nucleosides. The term oligonucleotide includes single-stranded and double-stranded forms unless otherwise indicated. The terms nucleic acid and oligonucleotide include, but are not limited to DNA molecules such as cDNA, genomic DNA or synthetic DNA and RNA molecules such as a guide RNA, messenger RNA or synthetic RNA.

The term "amplifying" is used broadly herein to include any means of increasing the number of molecules of a given nucleic acid sequence (e.g. of copying, or replicating a nucleic acid sequence), and includes exponential amplification mechanisms such as the well-known PCR and its known variants and multiple strand displacement (MDA), as well as non-exponential mechanisms such as RCA (exponential variants of RCA also exist). Like RCA, and unlike PCR, MDA is an isothermal reaction which does not require temperature cycling. In particular, the amplification method may involve extension (i.e. nucleotide chain extension) from a primer (i.e. primer-based amplification), and as noted above this may be a linear or an exponential amplification. Such amplification methods may employ sequence-specific primers, i.e. primers designed to hybridize to particular known sequences in the target fragment, or "random" primers may be used, such as hexamers, which, as is known in the art, are statistically likely to find complementary sequences with which to hybridize in any target fragments of a reasonable length.

The terms "guide RNA" generally refer to an RNA molecule (or a group of RNA molecules collectively) that can bind to a Cas protein and aid in targeting the Cas protein to a specific location within a target polynucleotide (e.g., a DNA). The term guide RNA may be abbreviated as "gRNA". A guide RNA can comprise a crRNA segment and a tracrRNA segment. The term "guide RNA segment" refers to a crRNA segment and/or a tracrRNA segment. As used herein, the term "crRNA" or "crRNA segment" refers to an RNA molecule or portion thereof that includes a polynucleotide-targeting guide sequence, a stem sequence, and, optionally, a 5'-overhang sequence. As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). The terms guide RNA and guide RNA segment also encompass a single guide RNA (sgRNA), where the crRNA segment and the tracrRNA segment are located in the same RNA molecule. The term guide RNA also encompasses, collectively, a group of two or more RNA molecules, where the crRNA segment and the tracrRNA segment are located in separate RNA molecules.

The term "scaffold" refers to the portions of guide RNA molecules comprising sequences which are substantially identical or are highly conserved across natural biological species. Scaffolds include the tracrRNA segment and the portion of the crRNA segment other than the polynucleotide-targeting guide sequence at or near the 5' end of the crRNA segment, excluding any unnatural portions comprising sequences not conserved in native crRNAs and tracrRNAs.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

DETAILED DESCRIPTION

There are several approaches to synthesize a large set of dual guides representing the designed complexity and desired dual guide fidelity (defined as appropriately paired dual guides). The present methods can include or be used in conjunction with the synthesis of single strand dual guides by massively parallel oligonucleotide synthesis, such as Oligonucleotide Library Synthesis (OLS) performed by Agilent.

The present methods provide a superior alternative to cloning the amplified oligonucleotides to assess "scrambling" of appropriately paired guide RNAs. Cloning would entail the picking thousands of bacterial clones containing recombinant molecules, purifying recombinant DNA molecules from these clones, and subsequently Sanger sequencing each of these molecules to obtain statistically significant data to suggest that "scrambling" of appropriately paired guide RNAs has not occurred. The present methods can employ Next Generation sequencing of amplified oligonucleotides as discussed herein, thus converting a procedure requiring weeks to perform into a method requiring less than a week.

FIG. 1 shows the general organization of a dual guide oligonucleotide construct. As used herein, "dual guide" refers to a molecule that has two or more sequences which encode a guide RNA segment (also referred to as guide RNA segment-encoding sequences). The exemplary construct of FIG. 1 is 285 bases in length, which is considerably longer than the upper limit of 100 bases that can be synthesized using conventional column-based methods. P1 and P2 refer to distinct promoters, CRISPR1 refers to a sequence encoding a first crRNA segment, Tracer1 refers to a sequence encoding a first tracrRNA segment, CRISPR2 refers to a sequence encoding a second crRNA segment and Tracer2 refers to a sequence encoding a second tracrRNA segment. The construct of FIG. 1 includes a separate promoter for each of the sequences encoding a guide RNA segment, allowing for eventual cloning into a vector that will replicate in recipient cells and be translated to a combined CRISPR1-Tracer-1 guide RNA molecule, and a CRISPR2-Tracer2 guide RNA molecule, respectively. These CRISPR guide RNAs can then direct Cas9 to cleavage sites within the genome being examined. A host of CRISPR-Tracer sets can be synthesized in parallel and then pooled. This set of molecules can be referred to as a dual guide pool or dual guide library.

When the quantity of each dual guide oligonucleotide in the pool is small, it may be desirable to amplify the dual guide oligonucleotides prior to cloning or other use. However, it has been found that dual guide oligonucleotides can become "scrambled" as a result of amplification by PCR, whereby instead of the CRISPR1-encoding sequence being appropriately paired with the CRISPR2-encoding sequence (that is, the CRISPR1-encoding sequence and the CRISPR2-encoding sequence are only present in the library when they are together on the same oligonucleotide construct), the CRISPR1-encoding sequence is mispaired with, for example, a CRISPR3-encoding sequence and/or others in the library (that is, a CRISPR1-encoding sequence and a CRISPR3-encoding sequence are mis-paired on the same oligonucleotide construct). It is highly desirable to use a dual guide library that contains few or essentially no mispaired gRNA segment-encoding sequences.

Identifying a scrambled vs. non-scrambled library of dual guide oligonucleotide constructs (i.e., determining if a dual guide library contains an unacceptable number of scrambled dual guide molecules) can be accomplished by different methods. For instance, single strand dual guides could be converted into double strand molecules, then the resulting dual guide library could be cloned into an appropriate vector. The resulting molecules could be transformed/transfected into recipient host cells. After selecting a desired number of clones, recombinant DNA could be isolated from the selecting clones, followed by Sanger Sequencing and data analysis for each of the selected clones. However, this method would be laborious and tedious, and to obtain a statistically significant confidence level that none of the cloned dual guides are scrambled, a very high number (likely to be thousands) of clones would have to be selected and analyzed. Such a method would likely require many weeks of effort.

The present disclosure provides an alternative method to obtain this same confidence level in determining whether a dual guide library is scrambled. By performing PCR on the single strand dual guides as described herein to convert them into dsDNA, the dsDNA can then be analyzed using massively parallel sequencing, also referred to as Next Generation (NextGen) sequencing. Such a combined method of library construction and NextGen sequencing can take less than a week to perform. Thus, the present disclosure can be used to identify scrambled and non-scrambled dual guide libraries, and to take appropriate action (i.e., delivering non-scrambled dual guide libraries to the end-user).

High Fidelity Amplification Enzymes

The present methods employ an amplification enzyme to amplify the oligonucleotides. In some embodiments, a processive proofreading DNA polymerase or a high-fidelity amplification enzyme is employed, such as PfuUltra II Fusion HS (Hotstart) DNA polymerase (PfuUltra II HS (Hotstart) DNA polymerase combines fusion polymerase technology with engineered PfuUltra DNA polymerase, hotstart antibody and proprietary ArchaeMaxx PCR enhancing factor to achieve extreme accuracy, high specificity, and long target-length capability while dramatically reducing overall PCR extension times. This enzyme formulation is also supplied as a "Master Mix"; a 2× formulation including an optimized PCR reaction buffer, magnesium, and dNTPs. Both are available from Agilent Technologies, Inc.), Herculase II fusion DNA polymerase (Agilent Technologies, Inc.), or other Pfu fusion polymerase, or Phusion DNA Polymerase (available from New England Biolabs) or other Phusion polymerase. A Pfu DNA polymerase is fused with a high affinity double-stranded DNA binding domain to form a Pfu fusion polymerase. A DNA-binding domain is fused to a different *Pyrococcus*-like proofreading polymerase to form a Phusion polymerase. Other high fidelity DNA polymerases and polymerase compositions are disclosed in Hogrefe et al. U.S. Pat. Nos. 7,932,070 and 9,181,534; Borns U.S. Pat. No. 7,960,157 (Agilent), as well as in Hogrefe et al. U.S. Pat. No. 6,734,293, Hogrefe U.S. Pat. Nos. 6,183,997 and 6,444,428, and Mathur U.S. Pat. No. 5,948,663 (Stratagene).

For PCR amplification, the amplification enzymes used in the present methods are thermostable, meaning they are stable to heat, heat resistant, and function at high temperatures, e.g., 50 to 90° C. The thermostable enzyme does not become irreversibly denatured (inactivated) when subjected to the elevated temperatures for the time of denaturation of double-stranded polynucleotides. The heating conditions for denaturation will depend, e.g., on the buffer salt concentration and the length and nucleotide composition of the polynucleotides being denatured, but typically range from 85° C., for shorter polynucleotides, to 105° C. for longer oligonucleotides and for a time depending mainly on the temperature and the polynucleotide length, typically from 0.25 minutes for shorter polynucleotides, to 4.0 minutes for longer polynucleotides. Higher temperatures may be tolerated as the buffer salt concentration and/or GC composition of the polynucleotide is increased. Preferably, the polymerase will not become irreversibly denatured at 90 to 100° C. A polymerase that does not become irreversibly denatured, according to the invention, retains at least 10%, or at least 25%, or at least 50% or more function or activity during the amplification reaction.

Amplification Mixture

In the present methods, an amplification mixture can be formed in order to amplify the oligonucleotides. The amplification mixture generally comprises a set of oligonucleotides, along with an amplification enzyme, deoxyribonucleotide triphosphates (dNTPs), and primers. In some embodiments, the amplification mixture could be sequestered in an emulsion, an example of which is described by Tatjana Schütze and Jörn Glökler ("Lab Times" 2011, 1: 50). In some embodiments, the amplification mixture is a non-emulsion mixture (e.g., a homogenous mixture or a mixture containing a single phase). It has been found that a non-emulsion amplification mixture is advantageous in the present methods.

In some embodiments, the amplification mixture comprises dimethyl sulfoxide (DMSO). In some embodiments, the amplification mixture comprises DMSO in an amount that is at least 3%, alternatively at least 4%, alternatively from 3% to 6.5% of the amplification mixture, in a volume/volume basis (v/v). In some embodiments, the amplification mixture comprises DMSO in an amount that is about 3%, about 3.5%, about 4%, about 4.5%, about 5%, about 5.5%, about 6% or about 6.5% v/v of the mixture. It is contemplated that any of the foregoing percentages can be combined to form a range.

In some embodiments, the oligonucleotides are present in the pool at a concentration of 2 nM, and the method further comprises diluting the oligonucleotides in the amplification mixture by a dilution of at least 1:10, alternatively at least 1:100, alternatively at least 1:1000, alternatively at least 1:2000, alternatively at least 1:4000, alternatively at least 1:8000, alternatively at least 1:16000. In some embodiments, the oligonucleotides are present in the pool at a concentration of 2 nM, and the method further comprises diluting the oligonucleotides in the amplification mixture by a dilution of alternatively at most 1:32000, alternatively at most 1:16000, alternatively at most 1:8000. It is contemplated that any of the foregoing dilution ratios can be combined to form a range.

In addition to the amplification enzyme, other components and/or conditions can be employed in the present methods to increase the fidelity of the amplification, such as the selection of desired dNTP concentration, units of enzyme used per reaction, and the ratio of $Mg^{2+}$ or other ions to dNTPs present in the amplification mixture.

$Mg^{2+}$ concentration affects annealing of primers to the template DNA by stabilizing the primer-template interaction, and it also stabilizes the replication complex of polymerase with template-primer. It can therefore also increase non-specific annealing and produce undesirable PCR products (produces multiple bands in analytical gel electrophoresis). When non-specific amplification occurs, $Mg^{2+}$ may need to be lowered or EDTA can be added to chelate $Mg^{2+}$ to increase accuracy and specificity of the amplification.

Other divalent cations such as $Mn^{2+}$ or $Co^{2+}$ can also affect DNA polymerization. Suitable cations for each DNA polymerase can be selected. Divalent cations are supplied in the form of a salts such $MgCl_2$, $Mg(OAc)_2$, $MgSO_4$, $MnCl_2$, $Mn(OAc)_2$, or $MnSO_4$. Suitable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cations required by DNA polymerase may be supplied by the potassium, sodium, ammonium, or lithium salts of either chloride or acetate. For KCl, the concentration can be between 1 and 200 mM, alternatively between 40 and 100 mM.

Deoxyribonucleotide triphosphates (dNTPs) are added as solutions of the salts of dATP, dCTP, dGTP, dUTP, and dTTP, such as disodium or lithium salts. In the present methods, suitable concentrations include the range of 1 µM to 2 mM, and 100-600 µM, although the concentration of the nucleotides may vary. For longer products, such as greater than 1500 bp, 500 µM each dNTP may be preferred when using a Tris-HCl buffer.

dNTPs chelate divalent cations, therefore the amount of divalent cations used may be selected based on the dNTP concentration in the reaction. Excessive amounts of dNTPs (e.g., larger than 1.5 mM) can increase DNA polymerase error rates and possibly inhibits activity of DNA polymerases. Lowering the dNTP concentration (e.g., to 10-50 µM) may therefore reduce error rate. PCR reaction conditions for amplifying larger template sizes may require a higher concentration of dNTPs.

A suitable buffering agent is Tris-HCl, such as at pH 8.3, or in the range of 8.0-8.8. The Tris-HCl concentration is from 5-250 mM, although 10-100 mM is most preferred. Another suitable buffering agent is Bicine-KOH, such as at pH 8.3, or in the range of 7.8-8.7.

Oligonucleotide primer concentrations in the amplification mixture can be selected, such as up to 3 µM of primers. High primer to template ratios can result in non-specific amplification and primer-dimer formation. Therefore it is usually recommended to optimize primer concentrations to avoid primer-dimer formation.

Cycling Parameters

The present methods generally comprise thermocycling an amplification mixture between a denaturing temperature, an annealing temperature, and an extension temperature. A sufficient number of cycles are performed to produce a library of oligonucleotide constructs. In some embodiments, the amplification mixture is thermocycled less than 30 times, alternatively less than 29, 28, 27, 26, 25, 24, 23, 22, 21, 20, 19, 18, 17, 16, 15, 14, 13, 12, 11, or 10 times. It is contemplated that any of the foregoing numbers can be combined to form a range for the number of thermocycles. For example, in some embodiments, the amplification mixture is thermocycled between 15 and 25 times, alternatively between 18 and 22 times, alternatively between 19 and 21 times.

Suitable denaturation temperatures and times are those sufficient to denature hybridized oligonucleotides in the amplification mixture. Denaturation temperatures of 80° C. and higher, such as 95° C. and higher, are commonly used. Denaturation time may be increased if template GC content is high. Higher annealing temperature may be needed when employing primers with high GC content or longer primers. Gradient PCR is a useful way of determining the optimum annealing temperature. Extension time should be extended for larger PCR product amplifications. However, extension time may need to be reduced whenever possible to limit damage to enzyme.

In some embodiments, the annealing temperature is between about 58° C. and about 72° C., for example, about 58° C., about 60° C., about 62° C., about 64° C., about 66° C., about 68° C., about 70° C., about 72° C. or about 74° C. It is contemplated that any of the foregoing temperatures can be combined to form a range. For example, in some embodiments, the annealing temperature is between 58° C. and 70° C., alternatively between 64° C. and 70° C.

In some embodiments, the amplification mixture is thermocycled between a denaturation temperature of 90° C. or higher, an annealing temperature as set forth above, and an extension temperature lower than the denaturation temperature and higher than the annealing temperature, for example greater than 70° C. and less than 90° C. In some embodiments, the thermocycle regimen comprises holding the amplification mixture at a denaturation temperature for a period of 20 seconds, and/or at an annealing temperature of 60° for 20 seconds, and/or at an extension temperature of 72° C. for 15 seconds.

In some embodiments, the number of thermocycles can be increased if a small quantity of template DNA is present or decreased if a high quantity of template DNA is present.

PCR Enhancing Factors and Additives

PCR enhancing factors may also be used to improve amplification efficiency. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). An exemplary PEF is Archae-Maxx polymerase-enhancing factor (Agilent). For Pfu DNA polymerase, a suitable PEF can be P45, P50, a complex of P50 and P45, or other PEF, as described in U.S. Pat. Nos. 6,183,997 and 7,625,725). The PEF can be provided in native form or as a recombinant protein. PEF can also be selected from the group consisting of: an isolated or purified naturally occurring polymerase enhancing protein obtained from an archeal source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR components may be selected to improve the accuracy and specificity of PCR reaction. For instance, EDTA less than 0.5 mM may be present in the amplification reaction mix. Additionally, detergents such as Tween-20 and Nonidet P-40 are often present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 μg/μl) can improve efficiency of PCR reactions. Betaine (0.5-2M) is also useful for PCR with high GC content templates and long DNA fragments. Tetramethylammonium chloride (TMAC, >50 mM), tetraethylammonium chloride (TEAC), and trimethylamine N-oxide (TMANO) may also be used. Test PCR reactions should be performed to determine optimum concentration of each additive mentioned above.

Oligonucleotide Pools and Libraries

The present methods can be used to amplify oligonucleotides of various sizes and structures and to form oligonucleotide libraries having different utilities. In some embodiments, a pool of oligonucleotides comprises a plurality of unique oligonucleotides. In some embodiments, a pool of oligonucleotides consists essentially of unique oligonucleotides. In some embodiments, a pool of oligonucleotides is synthesized by using Agilent's Oligo Library Synthesis (OLS) technology or other array-based synthesis technique. In some embodiments, the oligonucleotides of the pool are single strand DNA (ssDNA) molecules and/or are synthesized by OLS, though the pool of oligonucleotides can be generated by any suitable technique.

In some embodiments, a pool comprises at least 1000 unique oligonucleotides, alternatively at least 10,000 unique oligonucleotides, alternatively at least 20,000 unique oligonucleotides, alternatively at least 50,000 unique oligonucleotides, alternatively at least 60,000 unique oligonucleotides, alternatively at least 100,000 unique oligonucleotides. In some embodiments, the pool comprises up to 500,000 unique oligonucleotides, alternatively up to 1,000,000 unique oligonucleotides, or even more. It is contemplated that any of the foregoing numbers can be combined to form a range.

In some embodiments, the library members are oligonucleotide constructs. In some embodiments, the oligonucleotide library is a library of dual guide oligonucleotide constructs. In some embodiments, the oligonucleotide library is a library of dual guide oligonucleotide expression cassettes, where the expression cassettes contains a sequence to be expressed by a transfected cell and a regulatory sequence that controls such expression. In some embodiments, the library members are dual guide expression cassettes configured for expression of a plurality of guide RNA segments. For instance, the library members can be dual guide expression cassettes, each comprising a first promoter, a sequence encoding a first guide RNA segment downstream (in a 5' to 3' direction) from the first promoter, a second promoter, and a sequence encoding a second guide RNA segment downstream from the second promoter. The promoters and gRNA segment-encoding sequences can be arranged sequentially in a 5' to 3' direction, or in a 3' to 5' direction. The oligonucleotide construct is configured so that a promoter initiates transcription of a downstream sequence such as a gRNA segment-encoding sequence.

EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Embodiment 1. A method of amplifying a pool of oligonucleotides comprising providing a pool of oligonucleotides, wherein each of the oligonucleotides comprises a defined pair of sequences encoding guide RNA segments; forming an amplification mixture comprising the pool of oligonucleotides, an amplification enzyme, deoxyribonucleotide triphosphates (dNTPs), and primers; thermocycling the amplification mixture between a denaturing temperature, an annealing temperature, and optionally an extension temperature, a sufficient number of times to produce a library of oligonucleotide library members; wherein essentially all of the library members have one of the defined pairs of sequences encoding guide RNA segments and where designed guide RNA segments are not mispaired or "scrambled".

Embodiment 2. The method of embodiment 1, wherein at least 99.9% of the library members have one of the defined pairs of sequences encoding guide RNA segments.

Embodiment 3. The method of embodiment 1 or 2, wherein the oligonucleotides are dual guide expression cassettes comprising a first promoter, a sequence encoding a first guide RNA segment downstream from the first promoter, a second promoter, and a sequence encoding a second guide RNA segment downstream from the second promoter.

Embodiment 4. The method of any of the foregoing embodiments, wherein the amplification enzyme is PfuUltra II Fusion HS (Hotstart) DNA Polymerase [Agilent catalog numbers 600670, 600672 and 600647] or PfuUltra II Hotstart PCR Master Mix [Agilent catalog numbers 600850 and 600852], or Herculase II DNA Polymerase or Phusion DNA Polymerase or other amplification enzyme(s) with similar or identical characteristics to the aforementioned enzymes.

Embodiment 5. The method of any of the foregoing embodiments, wherein the oligonucleotides are amplified in a non-emulsion mixture.

Embodiment 6. The method of any of the foregoing embodiments, wherein the amplification mixture comprises DMSO in an amount from 3% to 6.5% v/v.

Embodiment 7. The method of any of the foregoing embodiments, wherein the annealing temperature is between about 58° C. and 70° C.

Embodiment 8. The method of any of the foregoing embodiments, wherein the amplification mixture is cycled 18 to 22 times.

Embodiment 9. The method of any of the foregoing embodiments, wherein the cycles comprise holding the amplification mixture at a denaturation temperature of at least 80° C. for 10 to 30 seconds, and at an annealing temperature between 58° C. and 70° C. for 10 to 30 seconds.

Embodiment 10. The method of any of the foregoing embodiments, wherein the cycles comprise holding the amplification mixture at a denaturation temperature of about 95° C. for about 20 seconds, and at an annealing temperature between 64° C. and 70° C. for about 20 seconds.

Embodiment 11. The method of any of the foregoing embodiments, wherein the oligonucleotides are present in the pool at a concentration of approximately 2 nM, and the method further comprises diluting the oligonucleotides in the amplification mixture at a dilution between 1:1000 and 1:32000.

Embodiment 12. The method of any of the foregoing embodiments, wherein the oligonucleotides of the pool are single strand DNA (ssDNA) molecules.

Embodiment 13. The method of any of the foregoing embodiments, wherein the oligonucleotides of the pool are synthesized by OLS.

Embodiment 14. The method of any of the foregoing embodiments, wherein the pool comprises at least 10,000 unique oligonucleotides.

Embodiment 15. A library of dual guide expression cassettes made according to any of the foregoing embodiments.

Embodiment 16. A library of oligonucleotide constructs, wherein each of the oligonucleotide constructs comprises a defined pair of sequences encoding guide RNA segments, wherein essentially all of the oligonucleotide constructs of the library have a predefined pair of sequences encoding guide RNA segments, and/or the library is essentially free of mispaired sequences encoding guide RNA segments.

Embodiment 17. The library of embodiment 16, wherein at least 99.9% of the oligonucleotide constructs of the library have a predefined pair.

Embodiment 18. A method to evaluate an oligonucleotide library comprising amplifying a pool of oligonucleotides according to the method of any of the foregoing embodiments to form a library of oligonucleotide constructs; and sequencing a number of members of the library by massively parallel sequencing.

Embodiment 19. The method of embodiment 18, wherein the number of sequenced members is sufficient to determine whether the library comprises one or more library members having a pair of sequences encoding guide RNA segments different from the defined pairs.

EXAMPLES

Example 1

In this example, a set of single-stranded DNA oligonucleotides was synthesized, amplified and evaluated. More specifically, oligonucleotides of 285 bases in length and having the general structure of FIG. 1 were synthesized on an array using Agilent's OLS technology. The oligonucleotides were pooled to form the set. Emulsion PCR (e-PCR) was used to amplify the ssDNA oligonucleotides to form double stranded DNA (dsDNA) molecules. In this amplification a few templates (oligonucleotides) were sequestered in each emulsion droplet.

Figure 2:
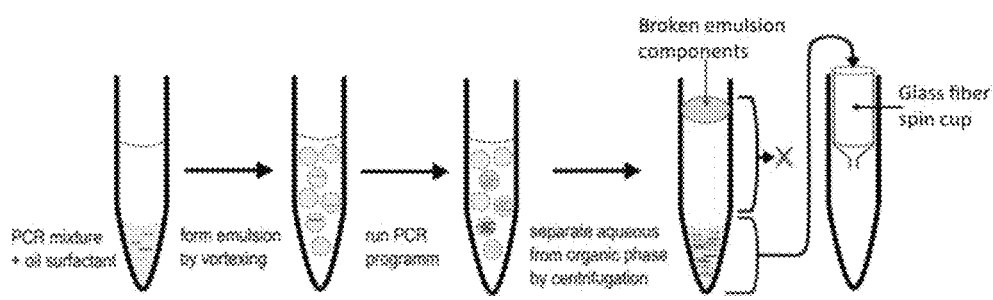
FIG. 2 is an illustration of an emulsion PCR process used for the examples.

FIG. 2 is an illustration of the emulsion PCR process. In this e-PCR technique, conventional aqueous PCR components were combined with an oil-surfactant mixture and converted into an emulsion by vigorous mixing. The following PCR components were combined in a final volume of 50 μL to form an amplification mixture containing the following components:

1. Agilent Herculase II enzyme 5×Buffer—10 μL
2. 5 μM each of primers complementary to the oligonucleotides—2 μL; 0.2 μM ea. final
3. dNTP's (100 mM stock)—1 μL; 0.5 mM ea. dNTP final
4. 250J OLS FAB library—1 μL neat
5. Herculase II enzyme—1 μL
6. 35 μL H$_2$O To each 50 μL reaction was added 73 μL TEGOSOFT cosmetic oil (Cetyl Ethylhexanoate), 20 μL mineral oil, and 7 μL of ABIL WE emulsifier (Polyglyceryl-4 Isostearate [and] Cetyl PEG/PPG-10/1 Dimethicone [and] Hexyl Laurate), followed by vortex mixing for 5 min. TEGOSOFT cosmetic oil and ABIL WE emulsifier are commercially available from Evonik Nutrition & Care GmbH. After mixing, the amplification mixture was subjected to the following thermocycling conditions:

1 cycle—95° C., 2 min.
20 cycles—95° C., 30 sec., 55° C., 30 sec., 72° C., 30 sec.
1 cycle—72° C., 3 min.

The emulsion was then degraded by addition of an aqueous breaking buffer ("BB"), followed by vigorous mixing and phase separation by centrifugation at 21K×g for 5 min. The liberated amplified dsDNA in the aqueous phase was purified away from PCR and emulsion components by a variety of techniques including magnetic beads and glass-fiber spin-cup technology. For example, following thermocycling, 300 μL BB was added to each reaction mixture, vortex mixed for 5 min., centrifuged at 21K×g for 5 min. and the aqueous phase collected for spin-cup purification. This procedure generated a 360 bp dsDNA library (Lane 1 in FIG.

3). The increased length (250 bases ssDNA library converted into a 360 bp dsDNA library) was due to extra bases included in the PCR primers.

A second PCR was performed on the dsDNA library. This PCR added nucleotide bases to the oligonucleotides to enable NextGen sequencing on a MiSeq instrument. As a result, the 360 bp oligonucleotides were increased in size to 460 bp (with 50 bp added at each end to make the oligonucleotides ready for sequencing with a MiSeq sequencing instrument). This PCR was performed in a final volume of 50 μL containing the following components:
1. Agilent Herculase II enzyme 5×Buffer—10 μL
2. 5 μM ea. primers for MiSeq sequencing—2 μL; 0.2 μM ea. final
3. dNTP's (100 mM stock)—1 μL; 0.5 mM ea. dNTP final
4. 5 μL lane 2 products
5. 31 μL $H_2O$
6. Herculase II enzyme—1 μL As before, to each 50 μL reaction was added 73 μL TEGOSOFT, 20 μL mineral oil and 7 μL of ABIL WE, followed by vortex mixing for 5 min. Thermocycling conditions were:
1 cycle—95° C., 2 min.
20 cycles—95° C., 30 sec., 55° C., 30 sec., 72° C., 30 sec.
1 cycle—72° C., 3 min.

Figure 3:
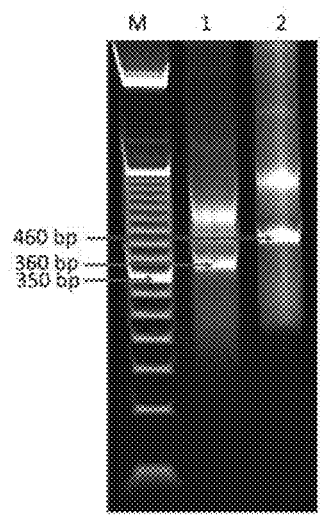
FIG. 3 shows an analysis of the lengths of oligonucleotides produced in Example 1.

Following thermocycling, 300 μL of BB was added to each reaction mixture, vortex mixed for 5 min., centrifuged at 21K×g for 5 min. and the aqueous phase collected for spin-cup purification. This procedure generated a 460 bp dsDNA library (Lane 2 in FIG. 3). The added length (460 bp vs. 360 bp) was due to extra bases included in the PCR primers.

Figure 4:
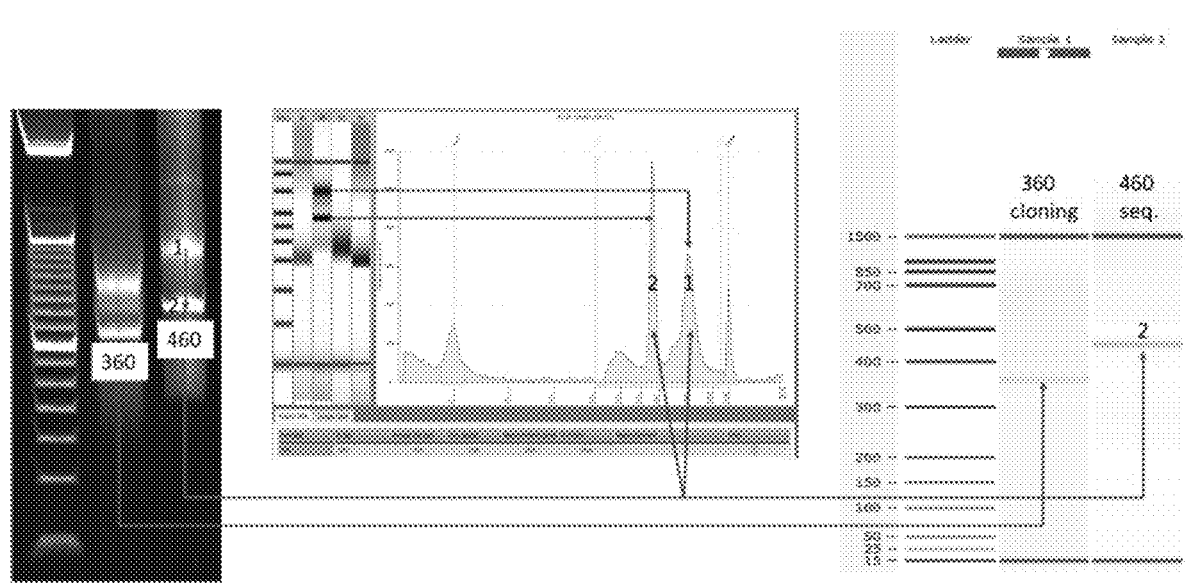
FIG. 4 shows three analyses of the purity and concentration of oligonucleotides produced in Example 1.

Prior to NextGen sequencing, the 460 bp product was examined by three analytical methods (TBE acrylamide gel, TapeStation, and BioAnalyzer) to determine purity and concentration. FIG. 4 shows the results from these three examinations. While the correct 460 bp product was present and in sufficient concentration for sequencing (labeled "2" in all three analytical tool sections of the figure), a higher molecular weight contaminant (labeled "1") was also present. The 360 bp precursor of the 460 bp product exhibited a similar higher molecular weight contaminant. NextGen sequencing of the contaminated 460 bp product indicated that the percentage of correct dual guide pairs was only 66%.

Example 2

This example sought ways of avoiding or minimizing the high molecular weight contaminants observed in Example 1, based on the hypothesis that this would improve correct dual guide pairing in an amplified library. To accomplish this goal, a series of experiments were performed in which e-PCR was replaced by o-PCR (o-PCR="open PCR", simply defined as "not using an emulsion to sequester PCR components"), a different PCR enzyme was used (as described in New England Biolab's Phusion DNA Polymerase, BioTechniques [2009], 4 [4]:857-866), DMSO was included as a component of the PCR mixture, the dual guide library template concentration was reduced, and the effects of different annealing temperature of the PCR thermocycling conditions were analyzed. A 50 μL volume of amplification mixture contained the following components:
1. 5 μM each of primers complementary to the oligonucleotides—2 μL; 0.2 μM ea. final
2. oligonucleotides 1 μL of 1:1000 dilution (2 pM)
3. DMSO—1.5 μL
4. Phusion Master Mix—25 μL
5. $H_2O$—20.5 μL Thermocycling conditions were:
1 cycle—98° C., 30 sec.
20 cycles—98° C., 10 sec., 58° C. to 74° C., 30 sec., 72° C., 30 sec.
1 cycle—72° C., 10 min.

The products of the amplification were pooled and spin-cup purified.

Figure 5:
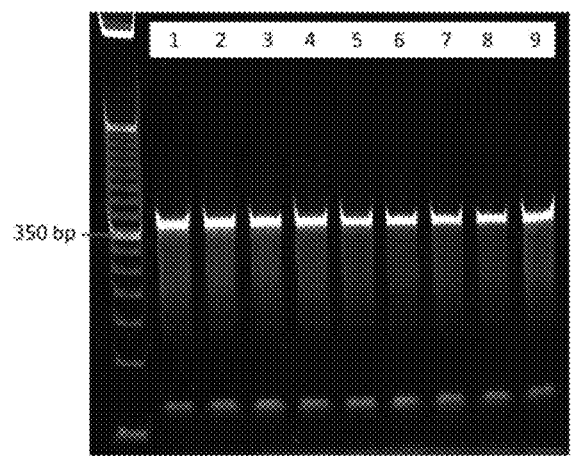
FIG. 5 shows an analysis of the lengths of oligonucleotides produced with different annealing temperatures in Example 2.

FIG. 5 shows the results of these combined changes in the amplification method. The amplification of the oligonucleotides in the pool produced the desired 360 bp precursor oligonucleotides. This example showed that annealing temperatures ranging from 58 to 74° C. did not alter the quality and quantity of the 360 bp precursor.

Spin-cup purification of the 360 bp precursor templates (FIG. 5) eliminated small molecular weight contaminants shown at the bottom of the gel image. Purified 360 bp was used for a series of o-PCR optimization experiments to generate sequencing-ready 460 bp products, as described in the following examples.

Example 3

In this experiment, a pool of 360-bp precursor oligonucleotides was used for a series of o-PCR amplifications to generate a library of 460-bp sequencing-ready oligonucleotides. This experiment studied the effect of dilution of the oligonucleotides in the amplification mixture. o-PCR amplifications were performed in a 50 μL volume containing the following components:
1. 5 μM each of primers complementary to the oligonucleotides—2 μL; 0.2 μL; 0.2 μM ea. final
2. oligonucleotides 1 μL of 1:1000 dilution (2 pM)
3. DMSO—1.5 μL
4. Phusion Master Mix—25 μL
5. $H_2O$—20.5 μL Amplifications were performed at oligonucleotide dilutions of 1:1000, 1:2000, 1:4000, 1:8000, 1:16000, 1:32000, 1:64000, 1:128,000 and 1:256,000 (lanes 2 through 9, respectively; lane 1 is a 50 bp marker DNA ladder). Thermocycling conditions were:
1 cycle—98° C., 30 sec.
20 cycles—98° C., 10 sec., 68° C., 30 sec., 72° C., 30 sec.
1 cycle—72° C., 10 min.

Figure 6:
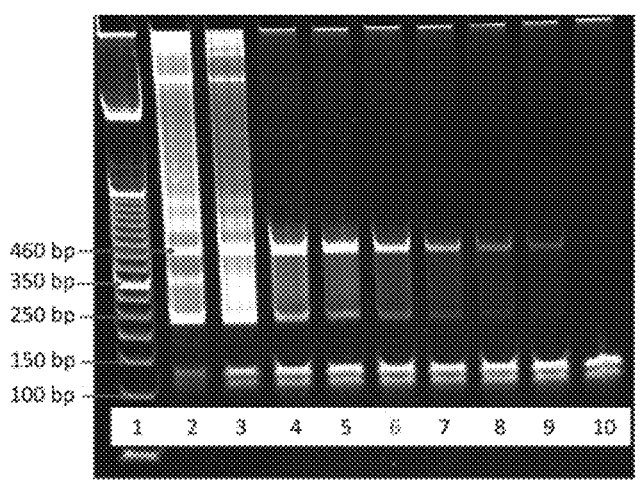
FIG. 6 shows an analysis of the lengths of oligonucleotides produced with different dilutions in Example 3.

FIG. 6 shows that dilution of the pool of 360 bp oligonucleotides reduced o-PCR 460 bp products and contaminants. Contaminants of 250 bp and between 150 and 100 bp were removed by spin-cup purification. A 1:4000 dilution (lane 3) was selected for additional experiments.

Example 4

Figure 7:
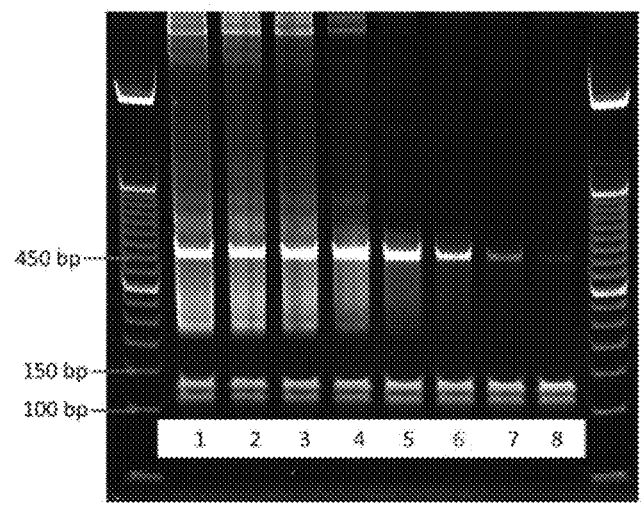
FIG. 7 shows an analysis of the lengths of oligonucleotides produced with different annealing temperatures in Example 4.

This experiment studied the effect of annealing temperatures in thermocycling the amplification mixture. Amplifications were performed as described in Example 3, with a 1:4000 dilution of oligonucleotides, and annealing temperatures of 58° C., 60° C., 62° C., 64° C., 66° C., 68° C., 70° C., and 72° C. (lanes 1 through 8, respectively). FIG. 7 shows analysis of the lengths of oligonucleotides produced in the various amplifications with different annealing temperatures. An annealing temperature of 68° C. (lane 6) was selected for additional experiments.

Example 5

Figure 8:
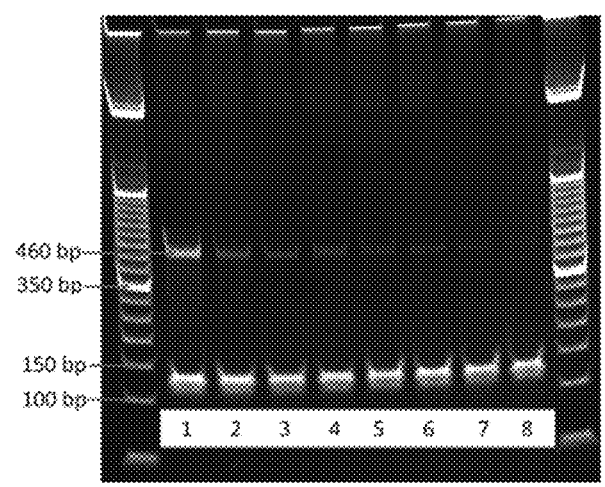
FIG. 8 shows an analysis of the lengths of oligonucleotides produced with different concentrations of DMSO temperatures in Example 5.

This experiment studied the effect of DMSO concentration in the amplification mixture. Amplifications were performed as described in Examples 3 and 4, with a 1:4000 dilution of oligonucleotides and an annealing temperature of 68° C. DMSO concentrations of 3%, 3.5%, 4%, 4.5%, 5%, 5.5%, 6% and 6.5% v/v were used (lanes 1 through 8, respectively). FIG. 8 shows an analysis of the lengths of oligonucleotides produced in the various amplifications with different concentrations of DMSO. A DMSO concentration of 4% v/v (lane 3) was selected for additional experiments. Even though the 460 bp product quantity was significantly reduced by increasing DMSO concentration from 3 to 3.5 percent, 4 percent was chosen to limit contaminants and perform multiple o-PCR experiments to generate sufficient 460 bp products for purification and NextGen sequencing.

Example 6

Figure 9A:
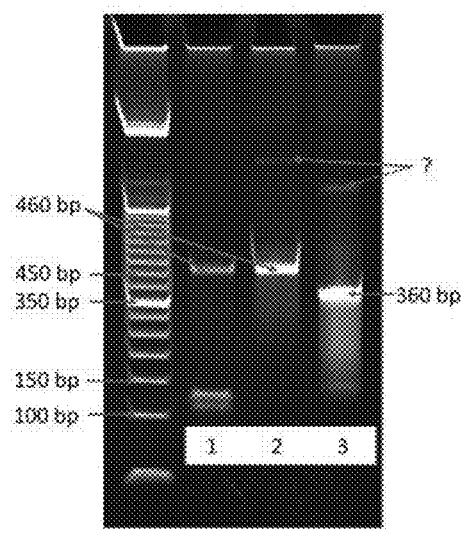
FIGS. 9A and 9B show analyses of the lengths of oligonucleotides produced at a given dilution and temperature in Example 6.

In this experiment, o-PCR amplifications were performed on a pool of 360 bp oligonucleotides in an effort to generate sufficient 460 bp products for purification and NextGen sequencing. Amplifications were performed as described in Examples 3, 4, and 5, with a 1:4000 oligonucleotides dilution, an annealing temperature of 68° C., and a DMSO concentration of 4% v/v. FIGS. 9A (gel electrophoresis) and 9B (Tapestation) show analyses of the lengths of oligonucleotides produced at a given dilution and temperature.

Figure 9B:
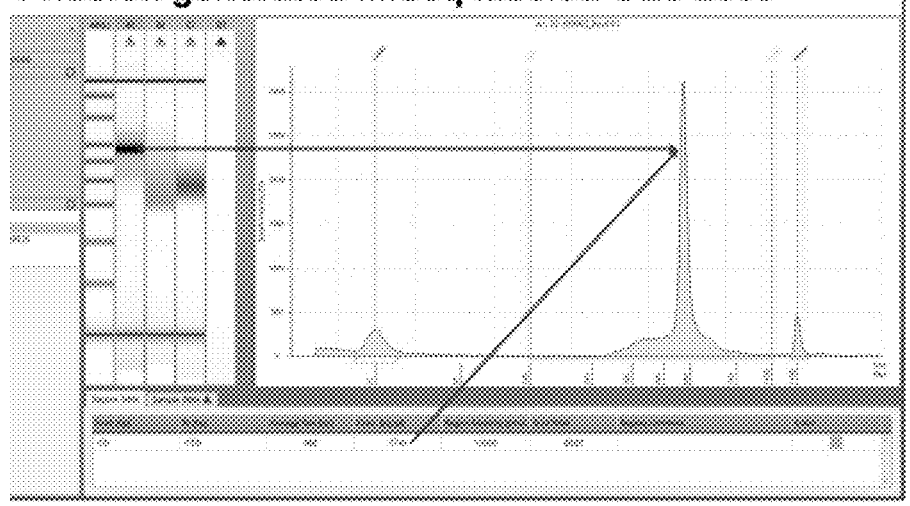

FIGS. 9A and 9B summarize the results of the optimization experiments. NextGen sequencing results demonstrated that the percentage of correct dual guide pairs in the amplified library increased to 99.99%, compared to 66% using a conventional PCR method. This dual guide library had few or essentially no scrambled library members.

Example 7

Figure 10:
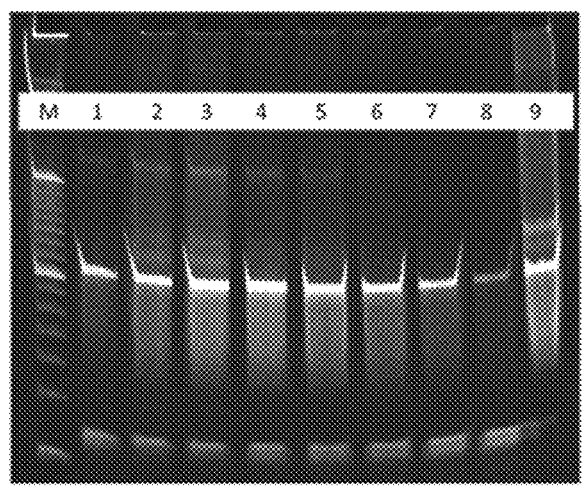
FIG. 10 shows analysis of oligonucleotides generated in Example 7.

This experiment identified another PCR enzyme for use in the present methods. o-PCR amplifications were performed on a pool of 360 bp oligonucleotides in an effort to generate sufficient 460 bp products for purification and NextGen sequencing. Amplifications were performed as described in Examples 3, 4, and 5, except that PfuUltra II Hotstart PCR Master Mix (Agilent) was used in the amplification mixture rather than Phusion DNA Polymerase. The o-PCR protocol was also adjusted in that DMSO was absent as an o-PCR component. FIG. 10 shows analysis of the oligonucleotides that were generated. Lane 1 shows products generated using undiluted library oligonucleotides. Lanes 2 through 8 correspond to library oligonucleotides dilutions of 1:2, 1:4, 1:8, 1:16, 1:32, 1:64, and 1:128 respectively. Lane 9 was a previously prepared 360 bp product to serve as an additional marker for correct 360 bp size. The correct size 360 bp product was synthesized in sufficient quantity at both 1:64 and 1;128 LIBRARY DILUTIONS.

Example 8

Figure 11:
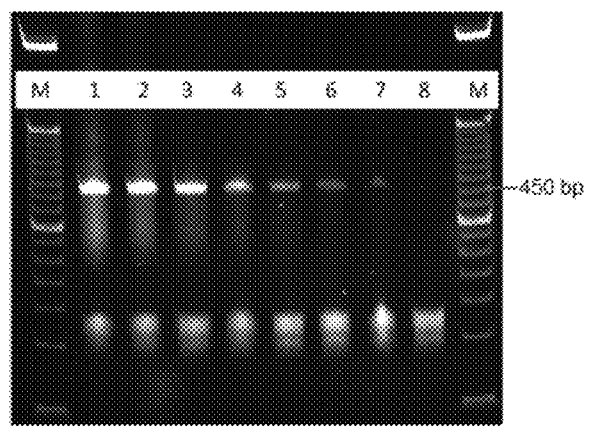
FIG. 11 shows analysis of the oligonucleotides which were generated in Example 8.

In this experiment, o-PCR amplifications were performed on a pool of 360 bp oligonucleotides in an effort to generate sufficient 460 bp products for purification and NextGen sequencing. Amplifications were performed as described in Examples 3, 4, and 5. A 1:128 dilution of the OLS dual guide library was chosen to produce sufficient purified 360 bp material for further development of the amplification protocol to generate the 460 bp o-PCR oligonucleotides that are ready for NextGen sequencing. FIG. 11 shows analysis of the oligonucleotides that were generated. Lanes 1 through 7 correspond to dilutions of 1:2, 1:4, 1:8, 1:16, 1:32, 1:64, and 1:128, respectively. Lane 8 had no template. FIG. 11 indicates that there was sufficient 460 bp material produced at the 1:128 dilution to warrant large scale o-PCR accumulation of this material for NextGen sequencing. Small molecular weight contaminants were removed by spin-cup purification.

Figure 12:
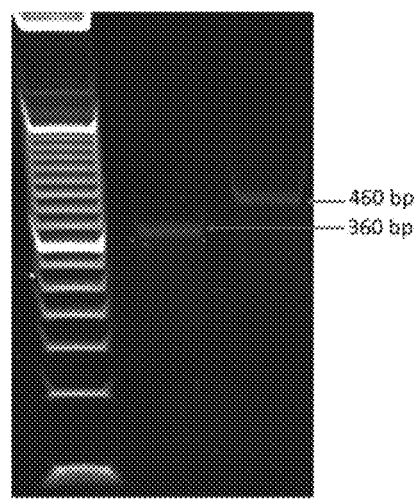
FIG. 12 shows further analysis of oligonucleotides generated in Example 8.

FIG. 12 further summarizes the results of this experiment, showing bands at 360 bp and 460 bp. While the band intensity is low, a sample of the 460 bp product was sequenced to determine the percent of correct oligonucleotide constructs. It was found that the percentage of constructs having correct dual guide pairs (that is, having one of the predefined pairs) was again 99.99%. These results indicate that a dual guide library essentially free of scrambled or mispaired library members was produced in this example.

Figure 13:
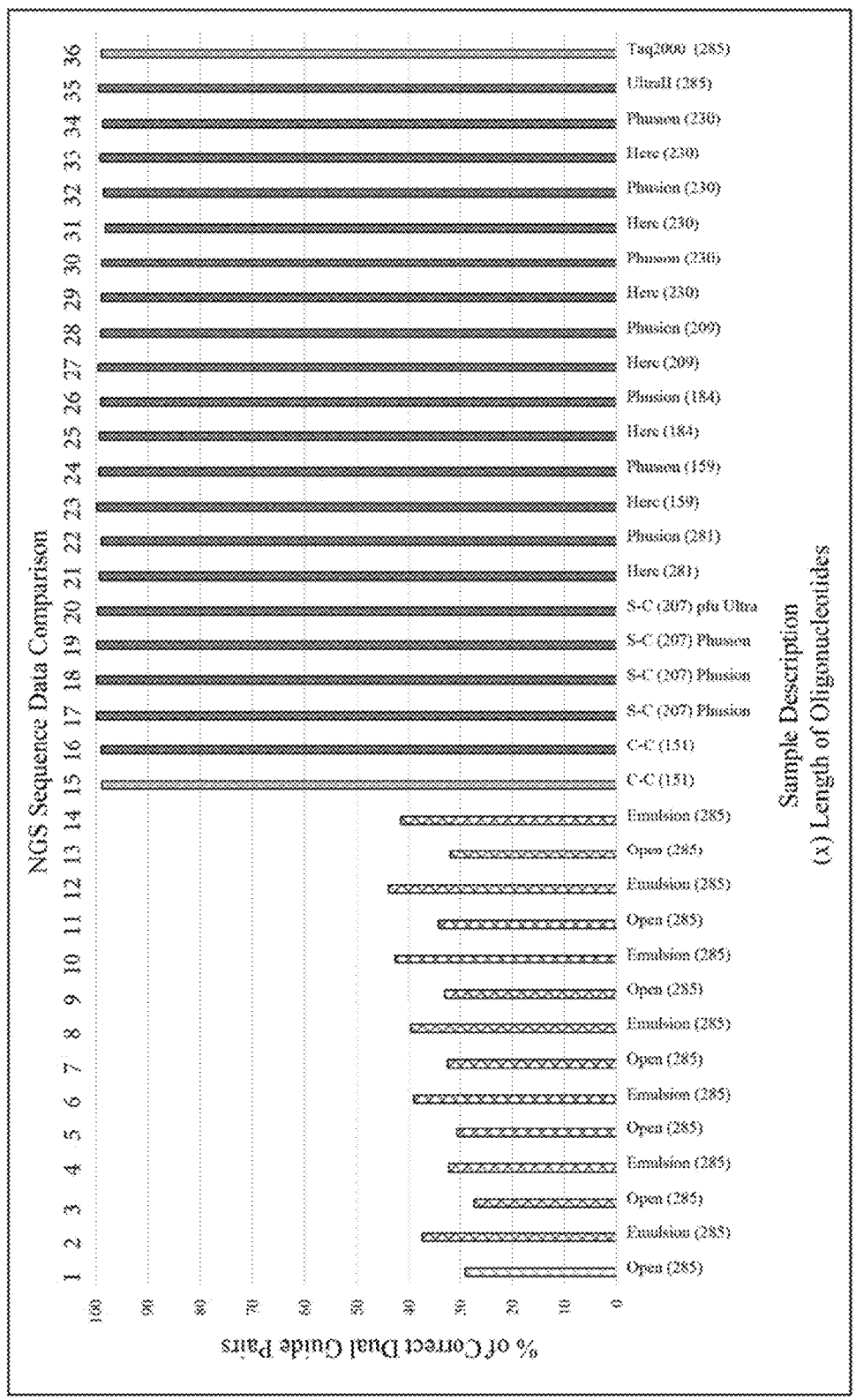
FIG. 13 shows percentages of correct pairs, as determined by NGS, in oligonucleotide pooled libraries after amplification by PCR.

FIG. 13 further summarizes results of these experiments showing percentages of correct pairs as determined by NGS in oligonucleotide pooled libraries after amplification by PCR. Bars 1 to 14 represent data obtained from samples amplified using a variety of standard PCR conditions (open and emulsion PCR reactions). Amplification yielded less than 50% corrected dual guide pairs, with some amplifications having less than 40% or less than 30%. Bars 15 to 36 represent data obtained from samples amplified using the present amplification methods, such as described in Examples 3, 4, and 5. The present amplification methods yielded close to 100% correct dual guide pairs.

The foregoing examples demonstrate that the present disclosure enables high fidelity amplification of a pool of oligonucleotides for use as a dual guide library in a CRISPR/Cas system. The present methods produced dual guide libraries where essentially all of the library members have one of the defined pairs of sequences encoding guide RNA segments. These examples also demonstrate that the present methods allows one to determine easily and quickly if a dual guide library retains correct dual guide pairs or whether it contains pairs that were not present in the original pool of oligonucleotides. The present methods are advantageous in significantly reducing the time and effort otherwise required for determining correct dual guide pairs in a library.

All patents and publications referred to herein are expressly incorporated by reference.

In view of this disclosure it is noted that the methods can be implemented in keeping with the present teachings. Further, the various components, materials, structures and parameters are included by way of illustration and example only and not in any limiting sense. In view of this disclosure, the present teachings can be implemented in other applications and components, materials, structures and equipment to implement these applications can be determined, while remaining within the scope of the appended claims.

What is claimed is:

1. A method of amplifying a pool of oligonucleotides comprising:
   providing a pool of oligonucleotides, wherein each of the oligonucleotides comprises a defined pair of sequences encoding guide RNA segments;
   forming an amplification mixture comprising the pool of oligonucleotides, an amplification enzyme, deoxyribonucleotide triphosphates (dNTPs), and primers;
   thermocycling the amplification mixture between a denaturing temperature, an annealing temperature, and an extension temperature, a sufficient number of times to produce a library of oligonucleotide library members, wherein the amplification mixture comprises DMSO in an amount from 3% to 6.5% v/v;

wherein at least 99.9% of the library members have one of the defined pairs of sequences encoding guide RNA segments.

2. The method of claim 1, wherein the oligonucleotides are dual guide expression cassettes comprising a first promoter, a sequence encoding a first guide RNA segment downstream from the first promoter, a second promoter, and a sequence encoding a second guide RNA segment downstream from the second promoter.

3. The method of claim 1, wherein the amplification enzyme is a processive proofreading DNA polymerase.

4. The method of claim 1, wherein the oligonucleotides are amplified in a non-emulsion mixture.

5. The method of claim 1, wherein the annealing temperature is between about 58° C. and 70° C.

6. The method of claim 1, wherein the amplification mixture is cycled 18 to 22 times.

7. The method of claim 1, wherein the thermocycles comprise holding the amplification mixture at a denaturation temperature of at least 80° C. for 10 to 30 seconds, and at an annealing temperature between 58° C. and 70° C. for 10 to 30 seconds.

8. The method of claim 1, wherein the thermocycles comprise holding the amplification mixture at a denaturation temperature of about 95° C. for about 20 seconds, and at an annealing temperature between 64° C. and 70° C. for about 20 seconds.

9. The method of claim 1, wherein the oligonucleotides are present in the pool at a concentration of approximately 2 nM, and the method further comprises diluting the oligonucleotides in the amplification mixture at a dilution between 1:1000 and 1:32000.

10. The method of claim 1, wherein the oligonucleotides of the pool are single strand DNA (ssDNA) molecules.

11. The method of claim 1, wherein the oligonucleotides of the pool are synthesized by array-based synthesis.

12. The method of claim 1, wherein the pool comprises at least 10,000 unique oligonucleotides.

13. A library of oligonucleotide library members made according to claim 1.

14. A library of oligonucleotide constructs, wherein each of the oligonucleotide constructs comprises a defined pair of sequences encoding guide RNA segments,
wherein at least 99.9% of the oligonucleotide constructs of the library have a predefined pair of sequences encoding guide RNA segments.

15. The library of claim 14, wherein each of the oligonucleotide constructs comprises a first promoter, a first crRNA segment, a first tracrRNA segment, a second promoter, a second crRNA segment, and a second tracrRNA segment.

16. A method to evaluate an oligonucleotide library comprising:
amplifying a pool of oligonucleotides according to the method of claim 1 to form a library of oligonucleotide constructs;
sequencing a number of members of the library by massively parallel sequencing.

17. The method of claim 16, wherein the number of sequenced members is sufficient to determine whether the library comprises one or more library members having a pair of sequences encoding guide RNA segments different from the defined pairs.

* * * * *